United States Patent
Scott et al.

(10) Patent No.: US 11,583,610 B2
(45) Date of Patent: Feb. 21, 2023

(54) SPRAY-DRIED THROMBIN AND METHODS OF USING AND MAKING SPRAY-DRIED THROMBIN

(71) Applicants: BAXTER INTERNATIONAL INC., Deerfield, IL (US); BAXTER HEALTHCARE SA, Glattpark (CH)

(72) Inventors: Alexander Wesley Scott, Chicago, IL (US); Paul Jeffrey Sanders, Greendale, WI (US); Alyssa Sanders, Mount Pleasant, WI (US); Adam Christopher Mercer, Chicago, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 82 days.

(21) Appl. No.: 16/956,968

(22) PCT Filed: Dec. 20, 2018

(86) PCT No.: PCT/US2018/066838
§ 371 (c)(1),
(2) Date: Jun. 22, 2020

(87) PCT Pub. No.: WO2019/133440
PCT Pub. Date: Jul. 4, 2019

(65) Prior Publication Data
US 2021/0379240 A1    Dec. 9, 2021

Related U.S. Application Data

(60) Provisional application No. 62/611,963, filed on Dec. 29, 2017, provisional application No. 62/771,936, filed on Nov. 27, 2018.

(51) Int. Cl.
*A61L 24/10* (2006.01)
*A61L 24/00* (2006.01)

(52) U.S. Cl.
CPC ......... *A61L 24/104* (2013.01); *A61L 24/0031* (2013.01); *A61L 24/108* (2013.01); *A61L 2400/04* (2013.01)

(58) Field of Classification Search
CPC .. A61L 24/104; A61L 24/0031; A61L 24/108; A61L 2400/04
See application file for complete search history.

(56) References Cited

U.S. PATENT DOCUMENTS

2008/0003272 A1    1/2008  Rapp et al.
2017/0157222 A1*   6/2017  Ilan ..................... A61K 9/1682

FOREIGN PATENT DOCUMENTS

| CN | 107754005 | | 3/2013 |
| DE | 19859611 | | 6/2000 |
| EP | 2575775 | * | 4/2018 |
| WO | 2011/151384 | | 12/2011 |
| WO | WO 2011/151384 | * | 12/2011 |
| WO | WO 2013/004838 | * | 1/2013 |
| WO | 2017/098493 | | 6/2017 |

OTHER PUBLICATIONS

Singapore Office Action for App. No. 11202005231R dated Feb. 8, 2022 (10 pages).
International Search Report for PCT/US2018/066838 dated Jul. 9, 2020 (7 pages).
International Search Report for PCT/US2018/066838 dated Apr. 8, 2019 (2 pages).
China Office Action for App. No. 20188080299.2 dated Nov. 29, 2021 (6 pages).
European Office Action for App. No. 18 834 224.0 dated Mar. 31, 2022 (6 pages).
Mexican Office Action for App. No. MX/a/2020/006856 dated Aug. 31, 2002 (3 pages).
Chinese Office Action for App. No. 201880080299.2 dated May 23, 2022 (8 pages).
Brazil Office Action for App. No. BR112020011034-5 dated Jul. 2, 2022 (4 pages).

* cited by examiner

*Primary Examiner* — Shirley V Gembeh
(74) *Attorney, Agent, or Firm* — K&L Gates LLP

(57) ABSTRACT

Spray-dried thrombin materials obtained from feedstock solutions comprising less than 5% by weight albumin and excluding trehalose or other excipients as well as methods of manufacturing the thrombin materials and methods of treating bleeding wounds are disclosed. The methods of use include applying reconstituted spray-dried thrombin topically to a bleeding site, optionally in conjunction with gelatin.

8 Claims, 5 Drawing Sheets

| Sample Type | Batch Number (1 vial of each) | Starting Content/Potency | RESULTS | |
|---|---|---|---|---|
| | | | Thrombin Potency by Time to Clot | TtC Recovery Time |
| Spray-dried thrombin | BAX-DEV-015 | 36480 IU/g | 32997 IU/g | 90.5 % |
| | BAX-DEV-016 | | 35542 IU/g | 97.4% |
| | BAX-DEV-017 | | 34164 IU/g | 93.7% |
| | BAX-DEV-018 | | 34750 IU/g | 93.0% |
| Feedstock solution | BAX-DEV-015 to -018 | 912 IU/mL | 864 IU/g | 94.8 % |

FIG. 2

| Sample Type | Batch Number (1 vial of each) | Starting Content/ Potency | RESULTS | | | | |
|---|---|---|---|---|---|---|---|
| | | | Mean Thrombin Potency by Time to Clot Month 0 | Mean Thrombin Potency by Time to Clot Month 1 | Mean Thrombin Potency by Time to Clot Month 2 | Mean Thrombin Potency by Time to Clot Month 3 | Mean Thrombin Potency by Time to Clot Month 6 |
| Spray-dried thrombin excluding trehalose | BAX-DEV-019 | 32456 IU/g | 33427 IU/g | 34777 IU/g | 34248 IU/g | 33062 IU/g | 33112 IU/g |
| Spray-dried thrombin comprising trehalose | BAX-DEV-020 | 1387 IU/g | 1229 IU/g | 1234 IU/g | 1242 IU/g | 1248 IU/g | 1212 IU/g |

FIG. 5

SPRAY-DRIED THROMBIN AND METHODS OF USING AND MAKING SPRAY-DRIED THROMBIN

BACKGROUND

Preventing excessive bleeding and promoting healing is an important aspect of many medical procedures. Preventing excessive bleeding can reduce transfusion rates and avoid minor complications in surgery, including cardiovascular surgery.

A variety of products are available that can act as hemostatic agents. For example, barrier materials have been proposed to assist in reducing bleeding as well, but many are made of non-biodegradable materials and can remain in the body with undesirable side effects. Additionally, it is often difficult to place and immobilize implants properly onto the bleeding site. Using non-solid anti-adhesive materials may also be problematic, because such materials often should be sufficiently fluid to enter and conform to the regions being treated, while simultaneously being sufficiently viscous enough to remain on the bleeding site until the tissue is healed. These objectives also have to be balanced with the requirements of biocompatibility and resorbability.

Certain hemostatic compositions currently used to prevent excessive bleeding and promote healing implement an aqueous carrier or form a hydrogel. These compositions may be delivered in the form of a powder and reconstituted at the time of use, the composition being biocompatible and permitting optimization of the release characteristics, including release rate, composition persistence, drug carrying capacity, product delivery characteristics (such as injectability), and the like. However, initial preparation of aqueous carrier or hydrogel composition often is time-consuming, which may be undesirable in certain environments such as emergency medicine situations. Moreover, the hemostatic compositions may require active agents, such as thrombin, which require additional preparation and delivery steps.

Certain compositions also require additional additives in order to improve reconstitution times, stability, or hemostatic performance. These additives, such as trehalose, increase the complexity of the product and can lead to problems for patients with intolerances to the additives.

For the above reasons, it is desirable to provide improved hemostatic compositions, methods of making these compositions, and related methods of using the compositions for preventing excessive bleeding and promoting healing following surgery or other trauma using powdered formulations that may be provided in powdered form and dissolved and reconstituted quickly and effectively. These compositions do not require additional additives in order to perform well.

SUMMARY

To improve medical treatment, especially to prevent excessive bleeding and promote healing, new hemostatic compositions and methods of making and using the same are described herein. The present disclosure seeks to implement new hemostatic compositions that eliminate undesirable features of current compositions, such as a long time to reconstitute, and the addition of ingredients that may not be tolerable to all patients.

The present disclosure sets forth methods for inhibiting bleeding by providing a spray-dried powdered thrombin material that is reconstituted and applied topically to a wound site in one embodiment. The thrombin material is aseptically spray-dried and does not require the addition of trehalose or a similar carbohydrate, e.g. a stabilizing sugar. The new and improved fast-reconstituting thrombin is spray-dried and contains an unexpectedly reduced amount of albumin.

In light of the disclosure herein, and without limiting the scope of the invention in any way, in a first aspect of the present disclosure, which may be combined with any other aspect listed herein unless specified otherwise, a hemostatic composition includes spray-dried thrombin and less than 5% by weight albumin, for example, less than 3% by weight albumin less than 2.5% by weight albumin, 1.5% to 2% by weight albumin, 2% to 2.5% by weight albumin, 2.5% to 3.5% by weight albumin, 2.5% to 3% by weight albumin, and/or 2.2% to 2.5% by weight albumin.

In a second aspect of the present disclosure, which may be combined with any other aspect listed herein unless specified otherwise, the hemostatic composition may be substantially free of carbohydrates.

In a third aspect of the present disclosure, which may be combined with any other aspect listed herein unless specified otherwise, the hemostatic composition may be substantially free of trehalose.

In a fourth aspect of the present disclosure, which may be combined with any other aspect listed herein unless specified otherwise, the hemostatic composition may be substantially free of mannitol.

In a fifth aspect of the present disclosure, which may be combined with any other aspect listed herein unless specified otherwise, a thrombin feedstock solution for spray-drying includes less than 5% by weight albumin prior to spray-drying, for example, less than 3% by weight albumin less than 2.5% by weight albumin, 1.5% to 2% by weight albumin, 2% to 2.5% by weight albumin, 2.5% to 3.5% by weight albumin, 2.5% to 3% by weight albumin, and/or 2.2% to 2.5% by weight albumin.

In a sixth aspect of the present disclosure, which may be combined with any other aspect listed herein unless specified otherwise, a spray-dried thrombin material may be obtained by spray-drying a thrombin feedstock solution as disclosed herein.

In a seventh aspect of the present disclosure, which may be combined with any other aspect listed herein unless specified otherwise, the thrombin may be aseptically spray-dried.

In an eighth aspect of the present disclosure, which may be combined with any other aspect listed herein unless specified otherwise, a spray-dried thrombin material includes 75% to 90% by weight total protein based on the total solids content of the material, for example 75% to 80% by weight total protein, 80% to 85% by weight total protein, and/or 85% to 90% by weight total protein.

In a ninth aspect of the present disclosure, which may be combined with any other aspect listed herein unless specified otherwise, a method for inhibiting bleeding includes reconstituting a spray-dried thrombin material as disclosed herein in less than sixty seconds, applying the reconstituted spray-dried thrombin material to a wound site; and, optionally co-administering a biologically compatible polymer to the wound site.

In a tenth aspect of the present disclosure, which may be combined with any other aspect listed herein unless specified otherwise, the biologically compatible polymer may be a gelatin.

In an eleventh aspect of the present disclosure, which may be combined with any other aspect listed herein unless specified otherwise, the gelatin may be cross-linked.

In a twelfth aspect of the present disclosure, which may be combined with any other aspect listed herein unless specified otherwise, the spray-dried thrombin material may be reconstituted in less than 1% NaCl by weight.

In a thirteenth aspect of the present disclosure, which may be combined with any other aspect listed herein unless specified otherwise, the spray-dried thrombin material may be reconstituted in less than thirty seconds, for example, in less than twenty seconds, in less then ten seconds, and/or in ten to twenty seconds.

In a fourteenth aspect of the present disclosure, which may be combined with any other aspect listed herein unless specified otherwise, the spray-dried thrombin material may not comprise trehalose.

In a fifteenth aspect of the present disclosure, which may be combined with any other aspect listed herein unless specified otherwise, a method of manufacturing a hemostatic composition includes aseptically spray-drying the thrombin feedstock solution as disclosed herein to obtain a spray-dried thrombin material.

In a sixteenth aspect of the present disclosure, which may be combined with any other aspect listed herein unless specified otherwise, the spray-dried thrombin material may maintain stability and potency in the absence of trehalose and/or mannitol.

Additional features and advantages of the disclosed compositions and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

Understanding that the figures depict only typical embodiments of the invention and are not to be considered to be limiting the scope of the present disclosure, the present disclosure is described and explained with additional specificity and detail through the use of the accompanying figures. The figures are listed below.

FIG. 2 is a table showing the thrombin potency as measured by time to clot assay for the spray-dried hemostatic composition comprising the present thrombin material in accordance with the formulation in Table 1. The materials comprise~2.2% albumin.

FIG. 5 is a table showing stability as measured by thrombin potency as measured by time to clot assay for spray-dried thrombin material compared to the same formulation also comprising trehalose.

DETAILED DESCRIPTION

Figure 1:
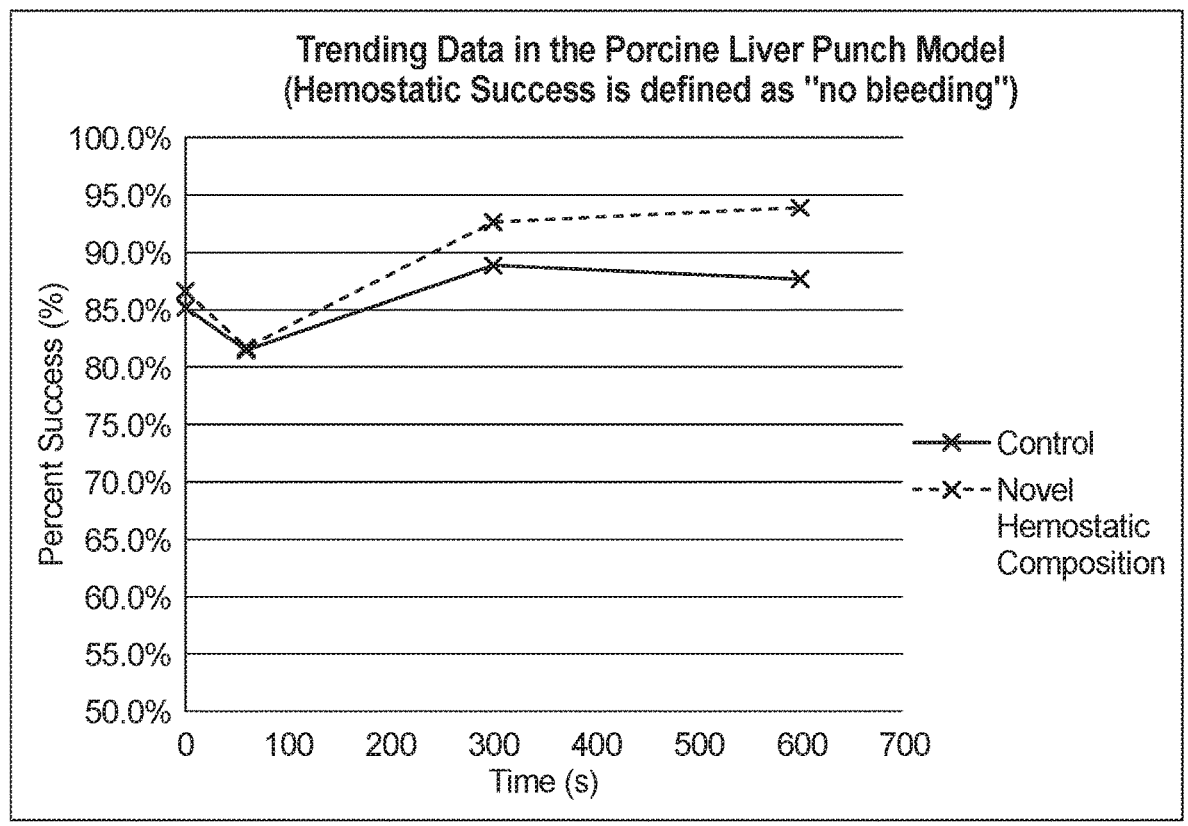
FIG. 1 is chart presenting the comparison between a control commercially available hemostatic composition comprising thrombin (not-spray dried and containing 5% albumin by weight) and the hemostatic composition comprising the present spray-dried thrombin material generated from feedstock containing approximately 2.5 wt. % albumin showing time to hemostatic success in a porcine liver punch model, where hemostatic success is defined as no bleeding occurring.

As discussed briefly above, this disclosure is, in various embodiments, directed to compositions, systems, and methods for inhibiting bleeding and promoting healing using a hemostatic composition comprising a spray-dried thrombin material and less than 5% albumin by weight. The hemostatic composition does not comprise trehalose, mannitol or other stabilizing sugars. The hemostatic composition may be co-administered with cross-linked or non-cross-linked powdered gelatin or other biologically compatible polymers. Similarly, this disclosure is directed to methods of making and using the hemostatic composition.

The hemostatic compositions disclosed herein may comprise spray-dried thrombin material. The thrombin may be aseptically spray-dried. In contrast to thrombin formulations that are not spray-dried, spray-dried thrombin material yields superior reconstitution times while maintaining thrombin activity as measured by time-to-clot measures. The spray-dried thrombin material may comprise 75% to 90% by weight total protein based on the total solids content of the material, for example 75% to 80% by weight total protein, 80% to 85% by weight total protein, and/or 85% to 90% by weight total protein. The spray-dried thrombin material may be in the form of substantially spherical particles.

The hemostatic composition may comprise 500 to 2000 IU/mL of thrombin, preferably 600 to 1000 IU/mL, and more preferably 700 to 1500 IU/mL.

The hemostatic composition may further comprise less than 5% albumin by weight. The composition may comprise less than 3% albumin, or less than 3% or 2.5% to 2% albumin or 2% to 2.5% or preferably 2.2% to 2.5%. Alternatively, the hemostatic composition may comprise 10 to 30 mg/mL of albumin, preferably 15 to 25 mg/mL.

The hemostatic composition may also comprise a commercially acceptable detergent. For example, the composition may comprise a nonionic surfactant such as Polysorbate 80.

The hemostatic composition may not include trehalose, mannitol or any other carbohydrate. Prior dried thrombin formulations required the addition of trehalose, mannitol or other carbohydrate to improve drying times and to maintain protein stability and retained activity. The present hemostatic compositions comprising spray-dried thrombin material maintain stability and retain high levels of thrombin activity without any need for a carbohydrate additive.

In some cases, the hemostatic compositions may further comprise an additional active agent. The active agent is selected from the group consisting of antibiotics, antineoplastic agents, bacteriostatic agents, bactericidal agents, antiviral agents, anesthetics, anti-inflammatory agents, hormones, anti-angiogenic agents, antibodies, enzymes, enzyme inhibitors, and neurotransmitters. In some cases, the active agent is an additional hemostatic substance.

The hemostatic compositions may be dissolved in NaCl or any other biologically acceptable diluent. The diluent may have suitable buffers, secondary binders, additives, preservatives, antioxidants, bioactive agents, or the like, added.

The hemostatic compositions of the present disclosure may be further combined with other materials and components, e.g., anti-caking agents, flow-enhancing agents, anti-static agents, and the like, such as zinc stearate, carbohydrates and alcohols, and other materials intended for other purposes, such as to control the rate of resorption.

The hemostatic compositions of the present disclosure may contain an active agent, in addition to thrombin. Exemplary active agents may include, but are not limited to, inorganic and organic biologically active molecules such as enzymes, enzyme inhibitors, antibiotics, antineoplastic agents, bacteriostatic agents, bactericidal agents, antiviral agents, hemostatic agents (e.g., fibrinogen and clotting factors), local anesthetics, anti-inflammatory agents, hormones, anti-angiogenic agents, antibodies, neurotransmitters, psychoactive drugs, drugs affecting reproductive organs and oligonucleotides, such as antisense oligonucleotides, or inorganic components such as hydroxyapatite, and ferric chloride. In some embodiments, the hemostatic compositions do not comprise fibrinogen. The composition may be substantially free of fibrinogen.

The hemostatic composition may be provided alone or with another powder and an appropriate diluent to form a flowable hemostat suitable for topical surgical applications. Alternatively, the hemostatic composition may be administered to a bleeding site as a powder hemostat, either alone or with another powder.

For example, the hemostatic composition may be co-administered with gelatin powder. The gelatin may be cross-linked or non-crosslinked. The hemostatic composition may also be administered with other biologically compatible polymers.

The co-administered biologically compatible polymer may be a protein, carbohydrate or carbohydrate derivative, non-biologic hydrogel-forming polymer or copolymer, or other biologically compatible polymers or combination of polymers which can form a hydrogel. Suitable polymers include, but are not limited to, proteins, such as gelatins, collagens, albumin, hemoglobin, fibronectin, fibrinogen, fibroin, elastin, keratin, laminin, casein, and the like, including sections thereof, such as fibronectin regions or collagen fragments. Suitable carbohydrate and carbohydrate derivative polymers include, but are not limited to, glycosaminoglycans, including, heparin, heparin sulfate, hyaluronic acid, chondroitin sulfate, keratin sulfate, and/or other extracellular matrix proteins, starches, celluloses, hemicelluloses, xylan, agarose, alginate, chitosan, and the like. Exemplary non-biologic hydrogel-forming polymers and copolymers include, but are not limited to, polyacrylates, polymethacrylates, polyacrylamides, polyvinyl polymers, polylactides-glycolides, polycaprolactones, polyoxyethylenes, polyethylene glycol, and copolymers thereof. Surface changes may further induce coagulation.

In some cases, the biologically compatible polymer is a cross-linked non-biologic hydrogel-forming polymer or copolymer selected from the group consisting of polyacrylates, polymethacrylates, polyacrylamides, polyvinyl polymers, polylactides-glycolides, polycaprolactones, polyoxyethelenes, and copolymers thereof.

In some cases, the cross-linked polymer is dispersed in a dried matrix of the optional non-cross-linked polymer. The optional non-cross-linked biologically compatible polymer may be a protein or a carbohydrate (or carbohydrate derivative) and may be the same polymer as the polymer which is cross-linked. Exemplary proteins include, but are not limited to, gelatin, collagen, albumin, elastin, keratin, and the like. Exemplary carbohydrates and carbohydrate derivatives include, but are not limited to, glycosaminoglycans, alginate, starch, cellulose, derivatives thereof, and the like. The non-cross-linked polymer may also be non-biological water soluble polymer, such as any of the hydrogel-forming polymers and co-polymers set forth above. An exemplary biologically compatible material that may be co-administered with the hemostatic compositions according to the present disclosure comprises a dry matrix of non-cross-linked gelatin polymer or a dry cross-linked gelatin polymer present as particles dispersed in the dry gelatin matrix.

The biologically compatible polymers with which the hemostatic compositions of the present disclosure may be co-administered may be formed from biologic and non-biologic polymers. Suitable polymers are described, for example, in U.S. Pat. Nos. 6,063,061, 6,066,325, 6,706,690, 7,435,425, 7,547,446, 8,092,820, 8,303,981, 8,357,378, 8,512,729, 8,603,511, 8,940,335, 9,084,728, and 9,408,945, the full disclosures of which are incorporated herein by reference and relied upon. Suitable biologic polymers include proteins, such as gelatin, soluble collagen, albumin, hemoglobin, casein, fibronectin, elastin, keratin, laminin, and derivatives and combinations thereof. One preferred use is the use of gelatin or soluble non-fibrillar collagen, more preferably gelatin, and exemplary gelatin formulations are set forth below. Suitable non-biologic polymers will be selected to be degradable by either of two mechanisms, i.e., (1) break down of the polymeric backbone or (2) degradation of side chains which result in aqueous solubility. Exemplary non-biologic hydrogel-forming polymers include synthetics, such as polyacrylates, polymethacrylates, polyacrylamides, polyvinyl resins, polylactides-glycolides, polycaprolactones, polyoxyethylenes, polyethylene glycol, and derivatives and combinations thereof.

For example, the hemostatic composition may be co-administered in either powder or flowable form along with a powdered non-gelatin matrix such as XL icodextrin. Alternatively the hemostatic composition may be co-administered in either powder or flowable form along with a powdered non-gelatin matrix mixed with a suitable diluent, such as saline or calcium chloride. The hemostatic composition may be administered in powder form along with powdered fibrinogen, or the hemostatic composition may be administered in flowable form along with reconstituted fibrinogen.

Suitable cross-linked polymers for co-administration with the hemostatic compositions according to the present disclosure are described in detail in U.S. Pat. No. 6,066,325, the full disclosure of which is incorporated herein by reference and relied upon. The biologically compatible polymers may be molecular cross-linked. The term "molecular cross-linked," may mean that the materials comprise polymer molecules (i.e., individual chains) which are attached by bridges composed of either an element, a group, or a compound, where the backbone atoms of the polymer molecules are joined by chemical bonds. Alternatively, the cross-linked polymers may be formed by non-covalent interactions such as electrostatic, ionic or hydrophobic. Cross-linking may be effected in a variety of ways.

Exemplary methods for producing molecular cross-linked gelatins are as follows. Gelatin is obtained (it may be pre-ground to a target size) and placed in an aqueous buffer to form a non-cross-linked hydrogel, typically having a solids content from 1% to 70% by weight, usually from 3% to 10% by weight. The gelatin is cross-linked, typically by exposure to either glutaraldehyde (e.g., 0.01% to 0.5% w/w, for at least overnight and preferably 15-25 hours and ideally 17-21 hours at 0 to 15° C. in an aqueous buffer maintaining the pH at 9-9.5), sodium periodate (e.g., 0.05 M, held at 0 to 15° C. for 48 hours) or 1-ethyl-3-(3-dimethylaminopropyl) carbodiimide ("EDC") (e.g., 0.5% to 1.5% w/w, overnight at room temperature), or by exposure to about 0.3 to 3 megarads of 7 or electron beam radiation. Prior to the exposure to the cross-linking agent, the gelatin is pre-warmed by heating to 30-35° C. for 15-25 minutes and then cooled below 10-20° C., ideally heated to 35° C. for 20 minutes for compositions including additives, or for 1 hour at 27° C. and then cooled for compositions without additives. Alternatively, gelatin particles may have a solids content of 1% to 70% by weight, usually 3% to 10% by weight, and cross-linked by exposure to a cross-linking agent, typically glutaraldehyde (e.g., 0.01% to 0.5% w/w, overnight at room temperature). In the case of aldehydes, the pH may be held from about 6 to 11, and in one preferred embodiment from 7 to 10. When cross-linking with glutaraldehyde, the cross-links appear to be formed via Schiff bases or via another reaction, which may be stabilized by subsequent reduction, e.g., by treatment with sodium borohydride. After cross-linking, the resulting granules may be washed in water and optionally rinsed in an alcohol and dried. Alternatively, the gelatin may be mechanically disrupted prior to or after cross-linking, and co-administered with the hemostatic compositions of the present disclosure.

As a further aspect of the present disclosure, hemoactive materials may be made by suspending particles of cross-linked biologically compatible polymer as described above in an aqueous medium. The aqueous medium is then dried to form a solid phase comprising the dried polymeric particles. Lyophilization (freeze-drying) is one drying technique. Air drying, heat-assisted drying, spray drying, fluid-bed drying, molding, and other methods could also be used under certain circumstances.

The biologically compatible polymer for co-administration may be separately sterilized or both the polymers and the hemostatic compositions of the present disclosure may be sterilized and subjected to processing carried out under aseptic conditions. Sterilization may occur via electronic-beam, γ-irradiation, or via ethylene oxide or other chemical sterilant or the like. Preferably, the hemostatic compositions of the present disclosure are aseptically spray-dried and do not require terminal sterilization.

The hemostatic compositions disclosed herein may be formed as powders, pellets, plugs, tubes, split tubes, cylinders, irregular or regular granules or particles, or the like. These may be provided without compaction in a loose powder with interstices. Such forms of the material may be produced sterilely (e.g., by aseptic processing) or sterilized and provided in sterile packs as part of kits. Sterilization may occur via electronic-beam, γ-irradiation, or via ethylene oxide or other chemical sterilant, or the like. In addition to the sterile packs containing the solid forms of the materials, the kits may also contain instructions for use setting forth methods for inhibiting bleeding by reconstituting the sterilized hemostatic compositions, and placing the reconstituted sterilized materials at a target site in tissue (e.g., a wound or other site of bleeding tissue) with a delivery device or delivery system.

The hemostatic compositions are sized and dimensioned such that the composition has a sub-unit or particle size in the range from 0.01 mm to 1 mm; or more specifically, from 0.01 mm to 0.1 mm.

Compositions according to the present disclosure may comprise dried hemostatic materials, including biologically compatible materials. The term "biologically compatible" may mean that the materials will meet the criteria in standard #ISO 10993-1 (International Organization for Standardization, Geneva, Switzerland). Generally, biologically compatible materials are free from pyrogenic substances and will not cause adverse biological effects when applied to human tissue. The compositions of the present disclosure may be resorbable. The term "resorbable" may mean that the compositions will degrade or solubilize when placed directly onto or into a target site in a patient's body over a time period of less than one year, usually from 1 day to 120 days.

The term by "hydrogel," may mean that the composition comprises a hydrophilic cross-linked biologic or non-biologic polymer, which absorbs a large quantity of water or an aqueous buffer. The hydrogels have little or no free water, i.e., water cannot be removed from the hydrogel by simple filtration.

The term "target site" may be the location to which the reconstituted hemostatic composition is to be delivered for therapeutic effect, e.g. the bleeding site. Usually, the target site will be the tissue location of interest. In some cases, however, the hemostatic material may be administered or dispensed to a location near the location of interest.

The hemostatic compositions may be provided as a finely divided or powdered dry solid, which may be disrupted by further comminution to provide particles having a desired size, usually being narrowly confined within a small range. Further size selection and modification steps, such as sieving, cyclone classification, etc., may also be performed. For the exemplary hemostatic compositions described hereinafter, the dry particle size may be in the range from 0.01 mm to 1.5 mm, and in one preferred embodiment from 0.05 mm to 1.0 mm. An exemplary particle size distribution is such that greater than 95% by weight of the particles are in the range from 0.05 mm to 0.7 mm. The powdered hemostatic compositions may be formed by spray drying. The particle size distribution may be further controlled and refined by conventional techniques such as sieving, aggregation, further grinding, and the like.

Figure 3:
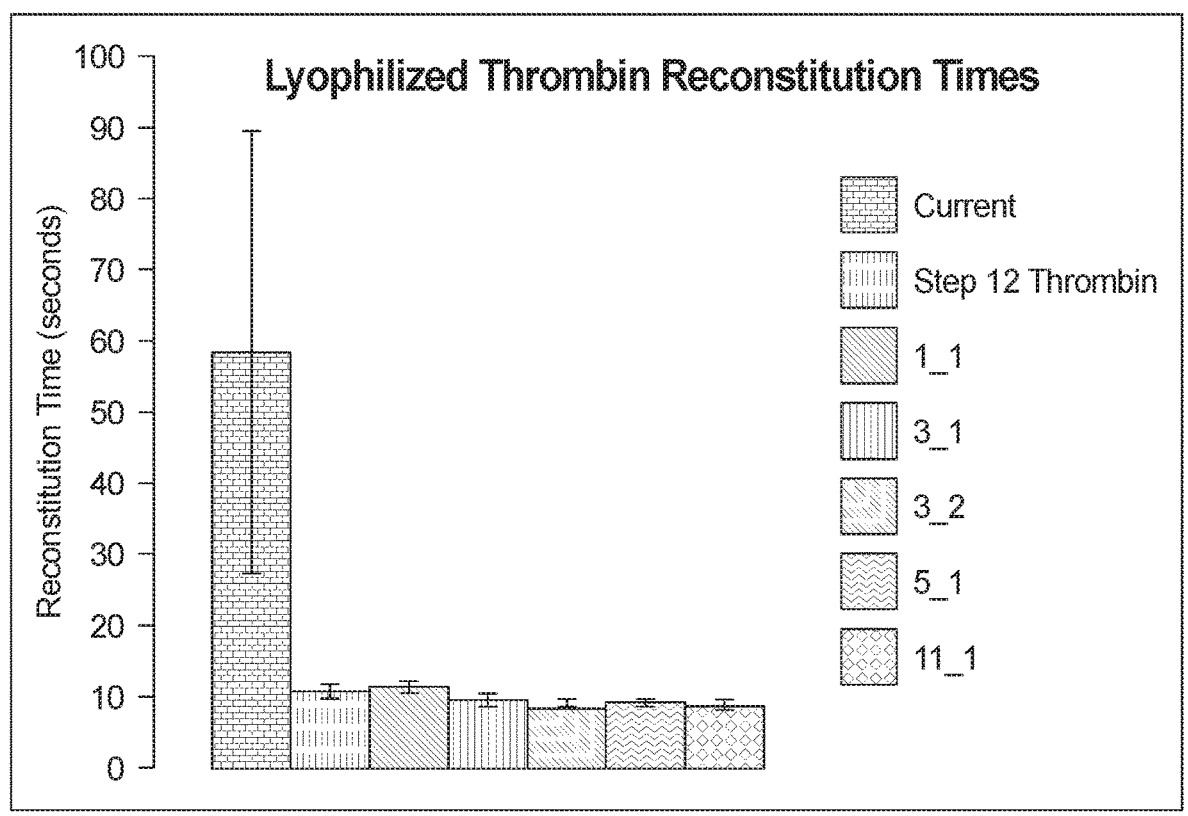
FIG. 3 is a chart presenting the reconstitution times for lyophilized hemostatic compositions comprising the present thrombin material and also comprising less than 3% albumin (the "Step 12 Thrombin") as compared to formulations such as "Current Thrombin" which comprises 5% albumin.

The hemostatic compositions comprising spray-dried thrombin material of the present disclosure may be reconstituted prior to use. The spray-dried thrombin material may be reconstituted in sodium chloride, calcium chloride or a similar diluent. In contrast to non-spray dried formulations and to formulations comprising 5% or more of albumin, the hemostatic compositions comprising spray-dried thrombin material of the present disclosure may be reconstituted in less than 60 seconds of time. As shown in FIG. 3, other thrombin materials requires a minute or more of reconstitution time, while the present hemostatic composition reconstituted in 30 seconds or less. Alternatively, the present hemostatic composition may be reconstituted in less than a minute, or in 5-30 seconds, or in 15-30 seconds.

The compositions of the present disclosure are particularly suitable for inhibiting bleeding (causing hemostasis) on an abraded or damaged tissue surface, e.g., any organ surface including the liver, spleen, heart, kidney, intestine, blood vessels, vascular organs, and the like.

Kits according to the present disclosure may comprise a granule or other form of the dried hemostatic compositions 1 of the present disclosure, such as pellets, powder, or the like. The materials are formed sterilely via aseptic processing. Alternatively, the materials may be terminally sterilized using 7-irradiation, ethylene oxide, electronic beam irradiation, and the like. While still in a sterile form, the materials will be packaged in a sterile package, such as a pouch, tube, tray, box, or the like. Instructions for use setting forth a method of reconstituting the hemostatic compositions and placing the compositions over tissue in the presence of blood, e.g., at a wound, or surgical site, may also be provided as part of the kit. An exemplary kit includes the dried hemostatic compositions (e.g., spray-dried thrombin material comprising less than 2.5% albumin and no trehalose) present in a syringe along with dried powdered gelatin, an applicator tip, a delivery device configured to be used with the syringe, and instructions for use.

In an aspect of the present disclosure, which may be combined with any other aspect listed herein unless specified otherwise, a method for inhibiting bleeding includes providing a hemostatic composition comprising spray-dried thrombin, reconstituting the hemostatic composition, and then applying it topically to a wound site.

In an aspect of the present disclosure, which may be combined with any other aspect listed herein unless specified otherwise, the spray-dried thrombin material is provided in conjunction with dry, cross-linked gelatin polymer particles. Alternatively it may be provided with dry, non-cross-linked gelatin polymer particles.

In an aspect of the present disclosure, which may be combined with any other aspect listed herein unless specified otherwise, the hemostatic composition comprising the spray-dried thrombin material also comprises albumin. The composition may comprise less than 5% albumin by weight, or 1.5% to 2% albumin or 2% to 2.5% or 2.5% to 3.5% or 2.5% to 3%, or preferably 2.2% to 2.5%.

In an aspect of the present disclosure, which may be combined with any other aspect listed herein unless specified otherwise, the hemostatic composition comprising the spray-dried thrombin material may not contain any carbohydrates. For example, the hemostatic composition may not contain trehalose. It also may not contain mannitol or any other stabilizing sugar. The hemostatic compositions reconstitute well and maintain stability and performance in the absence of trehalose and mannitol. The hemostatic compositions may be substantially free of trehalose and/or substantially free of mannitol.

In an aspect of the present disclosure, which may be combined with any other aspect listed herein unless specified otherwise, the hemostatic composition comprising the spray-dried thrombin material may comprise a detergent. The hemostatic composition may comprise a nonionic surfactant such as Polysorbate 80, preferably Tween-80.

In an aspect of the present disclosure, which may be combined with any other aspect listed herein unless specified otherwise, the hemostatic composition comprising the spray-dried thrombin material may be dissolved in a saline solution, or in a similar solution, or in water. It may be dissolved in a solution of less than 2% sodium chloride (NaCl) by weight, preferably less than 1%. The hemostatic composition in solution may also comprise 1 to 10 mg/ML of NaCl, preferably 2 to 7 mg/mL, or 3 to 6 mg/mL.

In an aspect of the present disclosure, which may be combined with any other aspect listed herein unless specified otherwise, the thrombin material is aseptically spray-dried.

In an aspect of the present disclosure, which may be combined with any other aspect listed herein unless specified otherwise, the spray-dried thrombin material retained similar activity as compared to its form prior to spray-drying, preferably 40% to 100% retained activity, or 45% to 95% or 70% to 90%, or 85% to 95% or 95% to 100%.

In an aspect of the present disclosure, which may be combined with any other aspect listed herein unless specified otherwise, the spray-dried thrombin material retained similar activity as compared to other commercially available thrombin formulations, such as FLOSEAL® VH S/D (also known as FLOSEAL® HEMOSTATIC MATRIX VH S/D, FLOSEAL® HEMOSTATIC MATRIX, and FLOSEAL®) (Baxter Healthcare Corporation), preferably 80% to 100% retained activity, or 90% to 100% or 95% to 100%.

In an aspect of the disclosure, which may be combined with any other aspect listed herein unless specified otherwise, bleeding may be inhibited by providing hemostatic composition comprising a spray-dried thrombin material, reconstituting the material, and applying it to a bleeding site along with a biologically compatible polymer such as a cross-linked gelatin.

In an aspect of the present disclosure, which may be combined with any other aspect listed herein unless specified otherwise, the hemostatic composition comprising spray-dried thrombin material may be reconstituted in less than 60 seconds, specifically, it may be reconstituted in less than 30 seconds, or preferably less than ten seconds.

In an aspect of the present disclosure, which may be combined with any other aspect listed herein unless specified otherwise, hemostatic compositions comprising spray-dried thrombin material may be manufactured by aseptic spray drying with less than 5% by weight of albumin, preferably less than 3% by weight and without the addition of trehalose or mannitol. The composition is substantially free of trehalose and mannitol.

In an aspect of the present disclosure, which may be combined with any other aspect listed herein unless specified otherwise, the hemostatic compositions may be provided independently. Alternatively, the hemostatic compositions may be provided as a sealant, or as a powdered hemostat, or in a preferred embodiment, as a flowable hemostat.

In an aspect of the present disclosure, which may be combined with any other aspect listed herein unless specified otherwise, the hemostatic compositions may be provided in formulation, or as a sealant. The hemostatic compositions may be provided in combination with fibrinogen. Alternatively the hemostatic compositions may be provided in the absence of fibrinogen, and be substantially fibrinogen-free.

EXAMPLES

Example 1—Method of Manufacturing Spray-Dried Thrombin Material

The spray dried thrombin material was generated from an initial frozen bulk drug substance (BDS) that was thawed overnight at 2-8° C. prior to spray drying with the composition given in Table 1. This formulation underwent vapor heat treatment and solvent/detergent treatment prior to spray drying.

TABLE 1

| Component | Concentration | Unit of Measure |
| --- | --- | --- |
| Thrombin | 920 | IU/mL |
| | Spec limit: 700-1400 | |
| Sodium Chloride | 4.1 | mg/mL |
| | Spec limit: 3.0-6.0 | |
| Human Serum Albumin | 22 | mg/mL |
| | Spec limit: 18-26 | |

A Buchi® Mini Spray Dryer (B-290) was used to generate powdered thrombin from the initial bulk drug substance.

Thrombin powder characterization was performed using aliquots of the spray dried material. Residual moisture (RM) analysis (reported as a percentage) was performed using coulometric Karl-Fischer titration. Particle size distribution (PSD) measurements were performed using a Malvern Mastersizer and results were reported as D-values.

Enzyme activity in the presence of human plasma was measured using a thrombin time-to-clot assay with the use of a Stago Start hemostasis analyzer. Spray dryer operating parameters (outlet temperature, nozzle gas pressure, and feed rate) and powder characterization results are given in Table 2.

TABLE 2

Spray Drying Parameters and Thrombin Powder Characterization

| Spray Drying Parameters | | | Powder Characterization | | | | | Enzyme Activity |
|---|---|---|---|---|---|---|---|---|
| | Nozzle | | | Bulk | PSD | | | |
| Outlet (° C.) | Gas Pressure (bar) | Feed Rate (mL/min) | RM (%) | Density (g/cc) | Dv10 (µm) | Dv50 (µm) | Dv90 (µm) | Recovery (%) |
| 78-80 | 1.0 | 4.39 | 2.9 | 2.1494 | 5.4 | 12.82 | 27.24 | 97.4 |

Example 2—Hemostatic Efficacy of the Present Hemostatic Compositions Comprising Thrombin Material as Compared to Commercially Available Preparation The hemostatic efficacy of the hemostatic composition comprising the present thrombin material was spray dried and reconstituted as a flowable hemostat to treat liver injuries in male domestic pigs (a porcine liver punch model) was evaluated. The control group was lyophilized rather than spray-dried.

Hemostatic success at 10 minutes after application was evaluated as to compare between the hemostatic composition and FLOSEAL® VH S/D (also known as FLOSEAL® HEMOSTATIC MATRIX VH S/D, FLOSEAL® HEMOSTATIC MATRIX, and FLOSEAL®) (Baxter Healthcare Corporation), a bovine-derived gelatin matrix combined with a human-derived thrombin solution. The FLOSEAL® product comprises thrombin material and comprises approximately 5% albumin.

The hemostatic composition comprised 920 IU/mL of thrombin, 4.1 mg/mL sodium chloride, 22.00 mg/mL human serum albumin, and 0.004 mg/mL of Tween-80.

For the study, 57 mg of the hemostatic composition in a 2000 IN/syringe was co-filled into a 5 mL male syringe with 0.73 g of sterilized, crosslinked bovine gelatin (FLOSEAL® granules).

The control composition (FLOSEAL® matrix), comprised 500 IU/mL of thrombin, 4.5 mg/mL of sodium chloride, and 50 mg/mL of albumin.

The FLOSEAL® matrix was prepared according to the manufacturer's Instructions for Use (Baxter Healthcare Corporation, 2014). The thrombin solution was prepared by attaching the prefilled sodium chloride solution syringe to the luer connector of the vial adapter. Then, the rubber stopper of the thrombin vial was pierced, and all contents of the sodium chloride solution were transferred to the thrombin vial. The thrombin vial was then vented and swirled until the thrombin was completely dissolved. FLOSEAL® VH S/D was prepared by filling the empty 5 mL syringe with thrombin solution to the indicated mark (4 mL) and then connecting the gelatin matrix syringe to the syringe containing the thrombin solution. The thrombin solution was then passed into the gelatin matrix syringe, and the mixture was transferred back and forth between the syringes for at least 20 passes. Prior to application, aliquots of 1 mL of the prepared FLOSEAL® material were dispensed into 3 mL syringes to provide an application volume of approximately 1 mL.

After preparation of the two materials, a 30 f 15 minute wait time before application of the hemostat was maintained throughout the study. In addition, 1 mL portions of the hemostatic matrix was applied per lesion within this 30 f 15 timeframe.

An assessment of time to hemostatic success was measured comparing the FLOSEAL® VH S/D product as the control against the novel hemostatic composition. Hemostatic success was defined as no bleeding. As shown in FIG. 1, by 600 seconds, the novel hemostatic composition had 93.9% hemostatic success while the control only had reached 87.7% hemostatic success.

Thus, under the conditions of the study, hemostatic efficacy of the novel hemostatic composition of the present disclosure was comparable to FLOSEAL® VH S/D.

Example 3—Thrombin Potency of Spray-Dried Thrombin

The thrombin potency of the novel hemostatic composition comprising the present thrombin material was evaluated by comparing spray-dried thrombin to a feedstock solution (control). Thrombin potency and content were measured by a time to clot method.

As shown in FIG. 2, the spray-dried thrombin maintained potency and content as compared to the feedstock solution.

Thus, under the conditions of the study, hemostatic efficacy of novel hemostatic composition of the present disclosure was comparable to the feedstock solution.

Example 4—Hemostatic Efficacy of Spray-Dried Thrombin Comprising Trehalose and Excluding Trehalose The hemostatic composition comprising spray-dried thrombin material and less than 3% albumin was compared to the same formulation also comprising trehalose.

The two formulations were compared by measuring thrombin potency and content via a time to clot method.

Surprisingly, the formulation substantially free of trehalose was comparable to the formulation comprising trehalose.

Example 5—Maintenance of Enzyme Activity of Spray-Dried Thrombin

Hemostatic compositions comprising lyophilized thrombin material, specifically, 708 IU/mL thrombin, 4.3 mg/mL NaCl and 1.7 wt % albumin (the "Step 12 formulation") were compared to various alternate formulations including one comprising 5 wt % albumin ("Control"), and to formulations comprising additional excipients such as trehalose (Formula 3_2 with 2% trehalose and Formula 3_1 with 4% trehalose) and mannitol and trehalose (Formula 5_1 with 2% trehalose and 3% mannitol).

Figure 4:
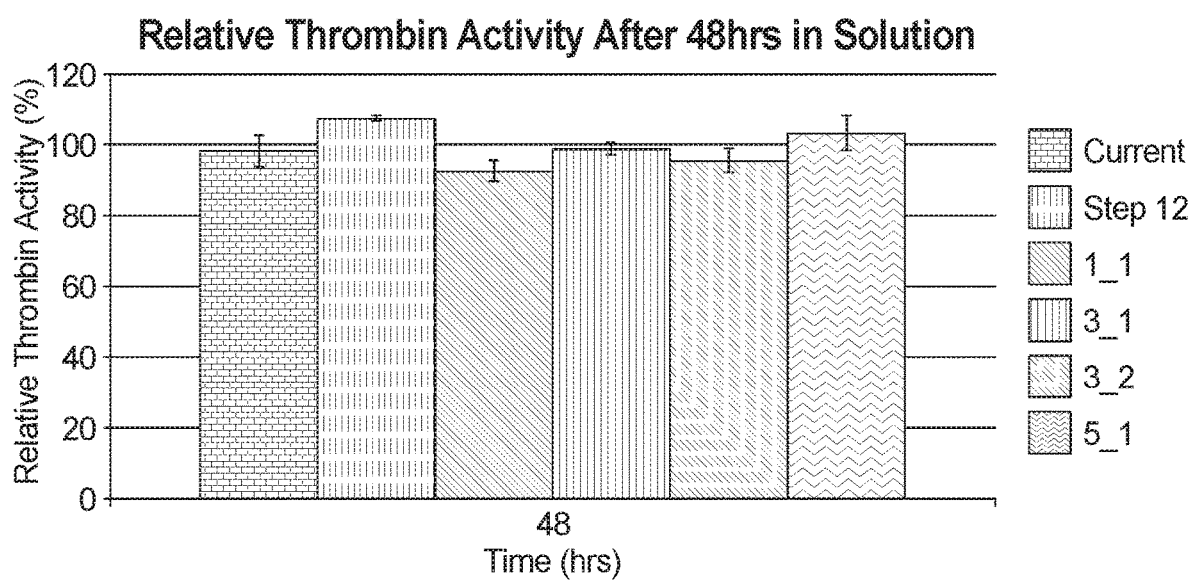
FIG. 4 is a chart presenting relative thrombin activity after 48 hours in solution for lyophilized hemostatic compositions comprising the present thrombin material comprising less than 3% albumin, as compared to a control formulation ("Current") comprising 5% albumin, and to formulations with excipients such as trehalose (3_1 comprises 4% trehalose while 32 comprises 2% trehalose) and trehalose and mannitol (5_1 comprises 2% trehalose and 3% mannitol).

As shown in FIG. 4, the Step 12 formulation according to the present disclosure had the best relative thrombin activity after 48 hours in solution (diluted 5 mL of 0.9% NaCl). Activity measurements were taken at the start, 24 hours later, and at 48 hours via a coagulation-based assay using pooled human plasma Thus, the hemostatic composition according to the present disclosure and without any added excipients performed best.

Example 6—Reconstitution Times of Spray-Dried Thrombin

Hemostatic compositions comprising spray-dried thrombin prepared in accordance with the formulation in Table 1 were tested for dissolution and reconstitution times. In contrast to non-spray dried formulations comprising 5% or more of albumin, the present hemostatic compositions had dissolution times of between 10 and 20 seconds.

Example 7—Stability of Spray Dried Thrombin Comprising Trehalose and Excluding Trehalose Hemostatic compositions comprising spray-dried thrombin material and less than 3% albumin (BAX-DEV-19) were compared to the same formulation also comprising trehalose (BAX-DEV-20) to assess stability of the formulations over a six month period. Stability was measured by thrombin potency as measured by a time-to-clot method.

The samples were prepared at lab scale using bulk spray drying of the thrombin in non-aseptic conditions. The hemostatic compositions were provided in 0.4 g fill in a 6 mL glass vial, in a double foil pouched with desiccant and stored between 2° C.-8° C.

As shown in FIG. 5, the spray dried thrombin without trehalose maintained stability over a six month period in a similar manner as the spray dried thrombin formulation with trehalose.

As used in this specification, including the claims, the term "and/or" is a conjunction that is either inclusive or exclusive. Accordingly, the term "and/or" either signifies the presence of two or more things in a group or signifies that one selection may be made from a group of alternatives.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention is claimed as follows:

1. A rapidly reconstitutable thrombin powder comprising thrombin and from about 2.2 to 2.5% by weight of albumin, said thrombin powder being reconstitutable in a saline diluent in less than 60 seconds, said thrombin powder being free of carbohydrate, trehalose and mannitol.

2. A rapidly reconstitutable thrombin powder as recited in claim 1 comprising 75%-90% by weight total protein based on total solids of the thrombin powder.

3. A rapidly reconstitutable thrombin powder as recited in claim 1, having a particle size of from about 0.01 mm to 0.1 mm.

4. A rapidly reconstitutable thrombin powder as recited in claim 1 prepared by spray drying.

5. A rapidly reconstitutable thrombin powder as recited in claim 1, prepared by aseptic spray drying.

6. A hemostatic composition comprising a spray-dried thrombin material and less than 2.2% to 2.5% by weight albumin, and wherein the hemostatic composition does not include carbohydrates.

7. The hemostatic composition according to claim 6, wherein the spray-dried thrombin material is aseptically spray-dried.

8. The hemostatic composition according to claim 6, wherein the spray-dried thrombin material comprises 75 to 90% by weight total protein based on the total solids content of the material.

* * * * *